US006973770B2

(12) United States Patent
Schnipke et al.

(10) Patent No.: US 6,973,770 B2
(45) Date of Patent: Dec. 13, 2005

(54) PALLET FOR SURGICAL STAPLING CARTRIDGE

(75) Inventors: Ronald J. Schnipke, Cloverdale, OH (US); David B. Erhart, Kalida, OH (US)

(73) Assignee: The Schnipke Family Limited Liability Company, Ottoville, OH (US)

( * ) Notice: Subject to any disclaimer, the term of this patent is extended or adjusted under 35 U.S.C. 154(b) by 0 days.

(21) Appl. No.: 10/747,940

(22) Filed: Dec. 30, 2003

(65) Prior Publication Data

US 2004/0148754 A1   Aug. 5, 2004

Related U.S. Application Data

(62) Division of application No. 10/032,727, filed on Dec. 28, 2001, now Pat. No. 6,729,119.

(51) Int. Cl.[7] .................... B29C 65/00; B29C 37/02; B23Q 3/00; A61B 17/04
(52) U.S. Cl. ................ 59/71; 59/77; 29/464; 29/811.2; 606/143; 227/19; 227/180.1
(58) Field of Search ........................ 59/71, 77; 29/464, 29/811.2, 818, 509; 606/143, 144; 227/19, 227/110, 120, 176.1, 180.1

(56) References Cited

U.S. PATENT DOCUMENTS

| | | | | |
|---|---|---|---|---|
| 3,751,902 A | * | 8/1973 | Kingsbury et al. | 59/71 |
| 3,894,174 A | * | 7/1975 | Cartun | 59/77 |
| 4,193,181 A | * | 3/1980 | Boulanger et al. | 29/509 |
| 4,612,933 A | * | 9/1986 | Brinkerhoff et al. | 227/19 |
| 4,714,187 A | * | 12/1987 | Green | 227/19 |
| 5,018,657 A | * | 5/1991 | Pedlick et al. | 227/19 |
| 5,392,509 A | * | 2/1995 | Cheswick | 29/818 |
| 5,653,928 A | | 8/1997 | Schnipke | |
| 5,836,147 A | | 11/1998 | Schnipke | |
| 5,911,353 A | * | 6/1999 | Bolanos et al. | 227/19 |
| 6,158,205 A | | 12/2000 | Schnipke et al. | |
| 6,729,119 B2 | * | 5/2004 | Schnipke et al. | 59/77 |

* cited by examiner

*Primary Examiner*—David B. Jones
(74) *Attorney, Agent, or Firm*—Jason H. Foster; Kremblas, Foster, Phillips & Pollick

(57) ABSTRACT

A means and method for inserting drivers into a surgical stapling cartridge, including a pallet that holds the cartridge firmly. The pallet has a central slot and laterally positioned lip members that are biased toward the slot. The cartridge is positioned in the slot and the lip members are released to extend their lips over the lateral flanges on the cartridge, thereby holding the cartridge in position. A finger extends into a recess formed at one end of the cartridge, thereby positively positioning the cartridge in the slot. The cartridge is released for removal by a tongue inserted between the lip members, thereby separating them by displacement.

14 Claims, 18 Drawing Sheets

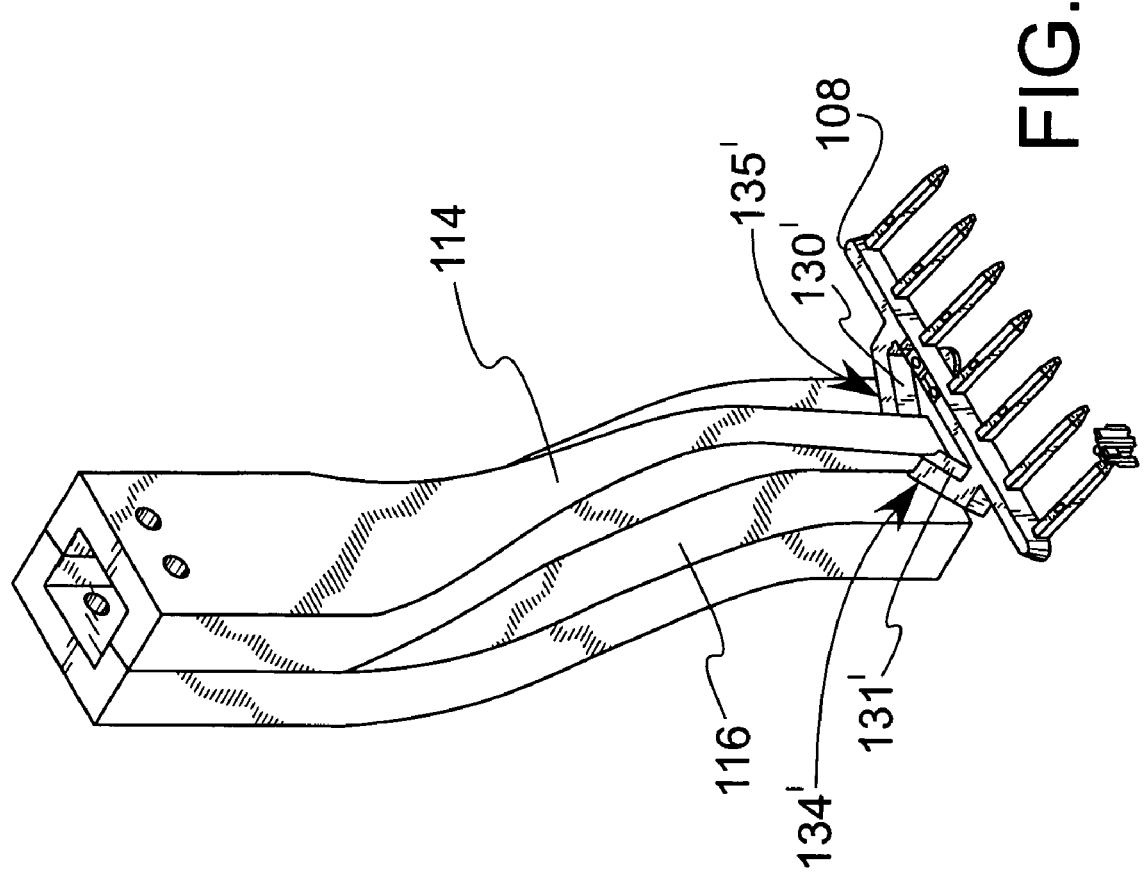

PALLET FOR SURGICAL STAPLING CARTRIDGE

This application is a divisional of U.S. application Ser. No. 10/032,727 filed Dec. 28, 2001 now U.S. Pat. No. 6,729,119.

(e) BACKGROUND OF THE INVENTION

1. Field of the Invention

This invention relates generally to a means and a method for loading a surgical stapling cartridge.

2. Description of the Related Art

It is known in the prior art mechanically to insert drivers into surgical stapling cartridges, as shown in U.S. Pat. No. 5,836,147 to Schnipke, U.S. Pat. No. 5,635,928 to Schnipke, and U.S. Pat. No. 6,158,205 to Schnipke et al., all of which are incorporated herein by reference. However, the mechanisms for this insertion require dexterity by trained people who are able to position the frames that contain the drivers and the cartridges, and actuate the machines to insert the tiny drivers into the precisely formed holes in the cartridges. After a fraction of the drivers are inserted by one machine, the cartridge is then manually transported to the next machine, which inserts another fraction of the drivers.

If any drivers are improperly inserted into a cartridge, or are not inserted, the cartridge is either discarded or repaired, which means that errors in insertion of the tiny parts can result in time and/or product lost. Such problems in manufacturing occur due to human error, and therefore it is desirable to mechanize the process to reduce the number of opportunities for error.

(f) BRIEF SUMMARY OF THE INVENTION

The invention is a moveable pallet used in a system in which robotic arms load cartridges. The pallet firmly holds a surgical stapling cartridge as drivers are inserted therein. The pallet comprises a base having a lower surface for seating on a conveyor. An elongated slot is formed in an upper surface of the base for holding the cartridge. A first cartridge-retaining lip member is movably mounted to the base on a first side of the slot, said first lip member being biased toward the slot. The lip member has a lip extending into the slot. A second cartridge-retaining lip member is mounted to the base on a second side of the slot. The second lip member is preferably moveable and biased toward the slot, and it has a lip extending into the slot.

A gap is formed between the first and second lip members to receive a tongue that is inserted upwardly through an aperture in the base. The tongue seats against opposing surfaces of the lip members and displaces the lip members away from the slot to release the cartridge. A finger is mounted to the base near a first longitudinal end of the slot, and extends into the slot for seating within a recess of the cartridge.

A preferred pallet has at least one tapered cavity formed in the lower surface of the base for receiving a foot for positively positioning the pallet horizontally. The preferred pallet also has at least one vertical registration surface that seats against at least two vertical registration arms for positively positioning the pallet vertically.

A tool is used for picking up a frame to which a plurality of drivers for the surgical stapling cartridge is mounted. The tool comprises a prime mover and a first finger drivingly linked to the prime mover. The first finger has a first pair of transverse planar panels formed in an inwardly facing surface of the first finger. The first pair of transverse planar panels is adapted to seat against corresponding surfaces on the driver frame. A second finger is connected to the prime mover, and has a second pair of transverse planar panels formed in an inwardly facing surface of the second finger that is substantially opposed to the inwardly facing surface of the first finger. The second pair of transverse planar panels is adapted to seat against corresponding surfaces of the driver frame.

A method of filling a surgical stapling cartridge is also contemplated. The method comprises holding firmly a cartridge in the above-described pallet, conveying the pallet to a first station, raising the pallet above the conveyor and inserting a plurality of drivers into the cartridge when the pallet is in a raised position. The pallet is next lowered back onto the conveyor and conveyed to a second station.

(g) BRIEF DESCRIPTION OF THE SEVERAL VIEWS OF THE DRAWINGS

FIG. 14 is a view in perspective illustrating the preferred end of arm tooling for gripping the frame to which drivers are mounted.

Figure 1:
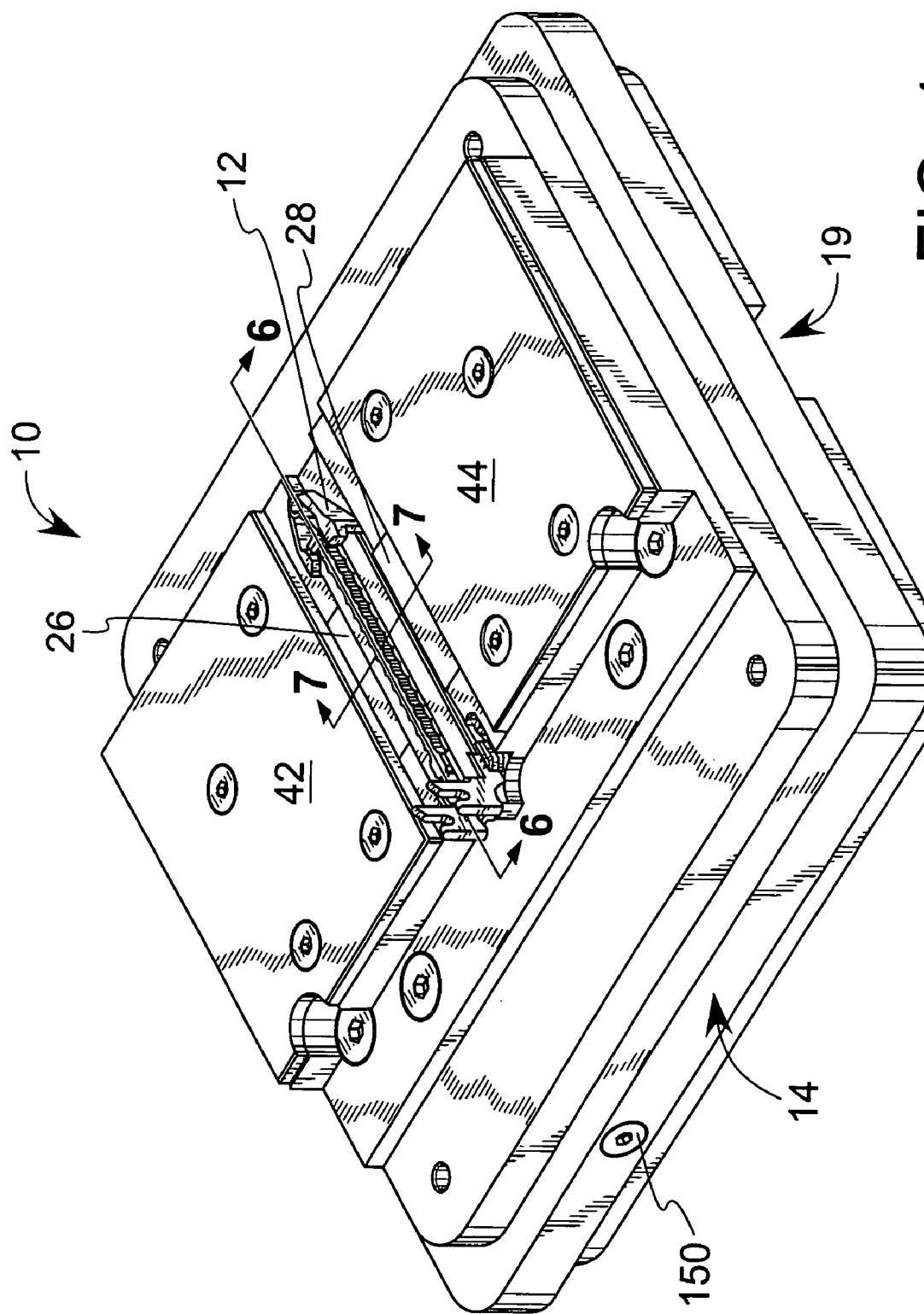
FIG. 1 is a view in perspective illustrating the preferred pallet with a cartridge in an operable position.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art.

(h) DETAILED DESCRIPTION OF THE INVENTION

The preferred pallet 10 is shown in FIG. 1 with a surgical stapling cartridge 12 mounted therein in an operable position. The pallet 10 is essentially made up of two components: the cartridge holder 20 shown in FIG. 2, and the base 14 shown in FIGS. 3 and 4. The base 14 is made of two subcomponents: the plate 16 and the ring 18. The plate 16 and the components of the cartridge holder 20 are preferably made of steel. The plate 16 forms a rigid frame to which the other components of the pallet 10 attach. The ring 18 is preferably made of a low friction polymer, such as is sold in association with the trademark DELRIN. The ring 18, plate 16 and the cartridge holding apparatus 20 are securely fixed together, such as by screws.

Figure 5:
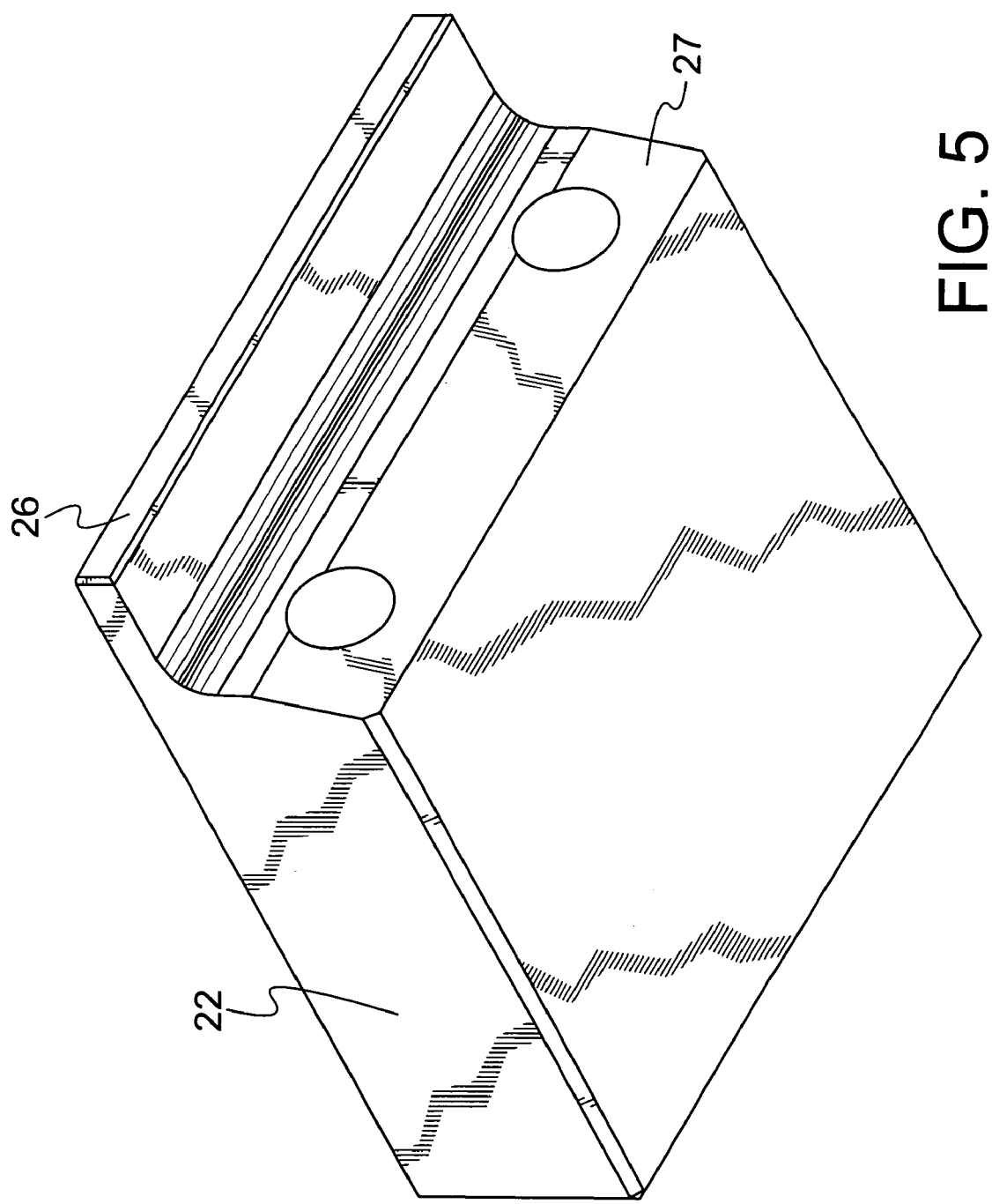
FIG. 5 is a view in perspective illustrating a lip member.

The lip members 22 and 24, both essentially identical to the lip member 22 shown in FIG. 5, are mounted in the chambers 32 and 34, respectively, formed in the cartridge holder 20. The lip members 22 and 24 have lips 26 and 28, respectively, both essentially identical to the lip 26 shown in FIG. 5. Each of the lip members is housed in its respective chamber with the lip member seating against the surfaces that define the chamber, but with the ability of the lip members to be displaced laterally toward and away from the slot 40. Each lip member is biased toward the slot 40, such as by coil springs. The cover panels 42 and 44 keep the lip members from coming out of the chambers, but permit the lip members to slide within the chamber.

Figure 2:
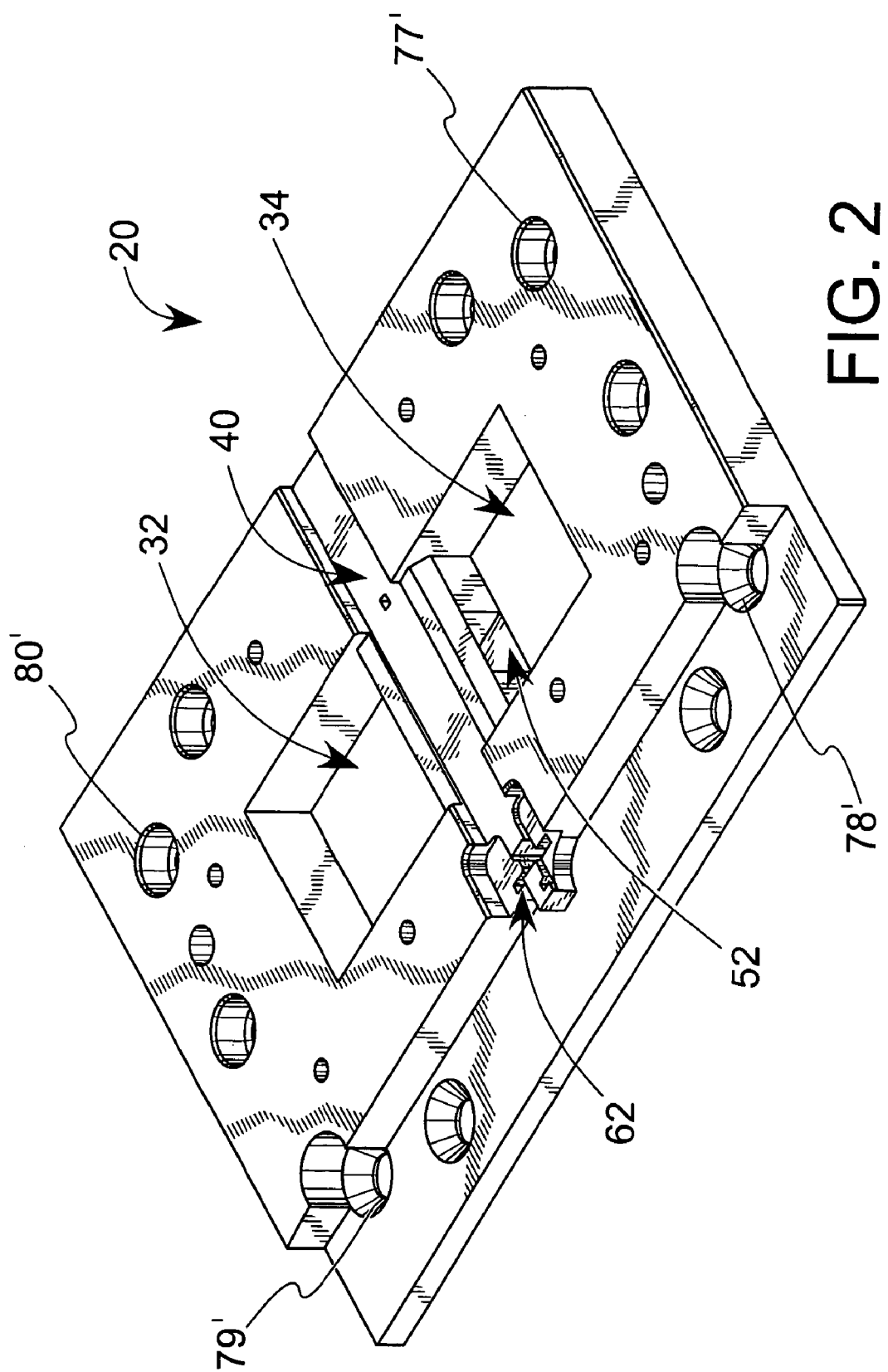
FIG. 2 is a view in perspective illustrating the cartridge holder, which is a component of the pallet.

In their operable position show in FIG. 1, the lips 26 and 28 extend from the chambers 32 and 34 into the slot 40, which is the region of the pallet 10 in which the cartridge 12 is held when it is mounted in the pallet 10 (see FIG. 2). The cartridge 12 is restrained in the slot 40 by the lips 26 and 28 extending over the lateral flanges on the cartridge 12, which lateral flanges are conventional for surgical stapling cartridges of the type shown. Thus, the cartridge is held firmly and rigidly to the pallet 10, and cannot be removed without either breaking the flanges or retracting the lips 26 and 28 away from the flanges.

Figure 8:
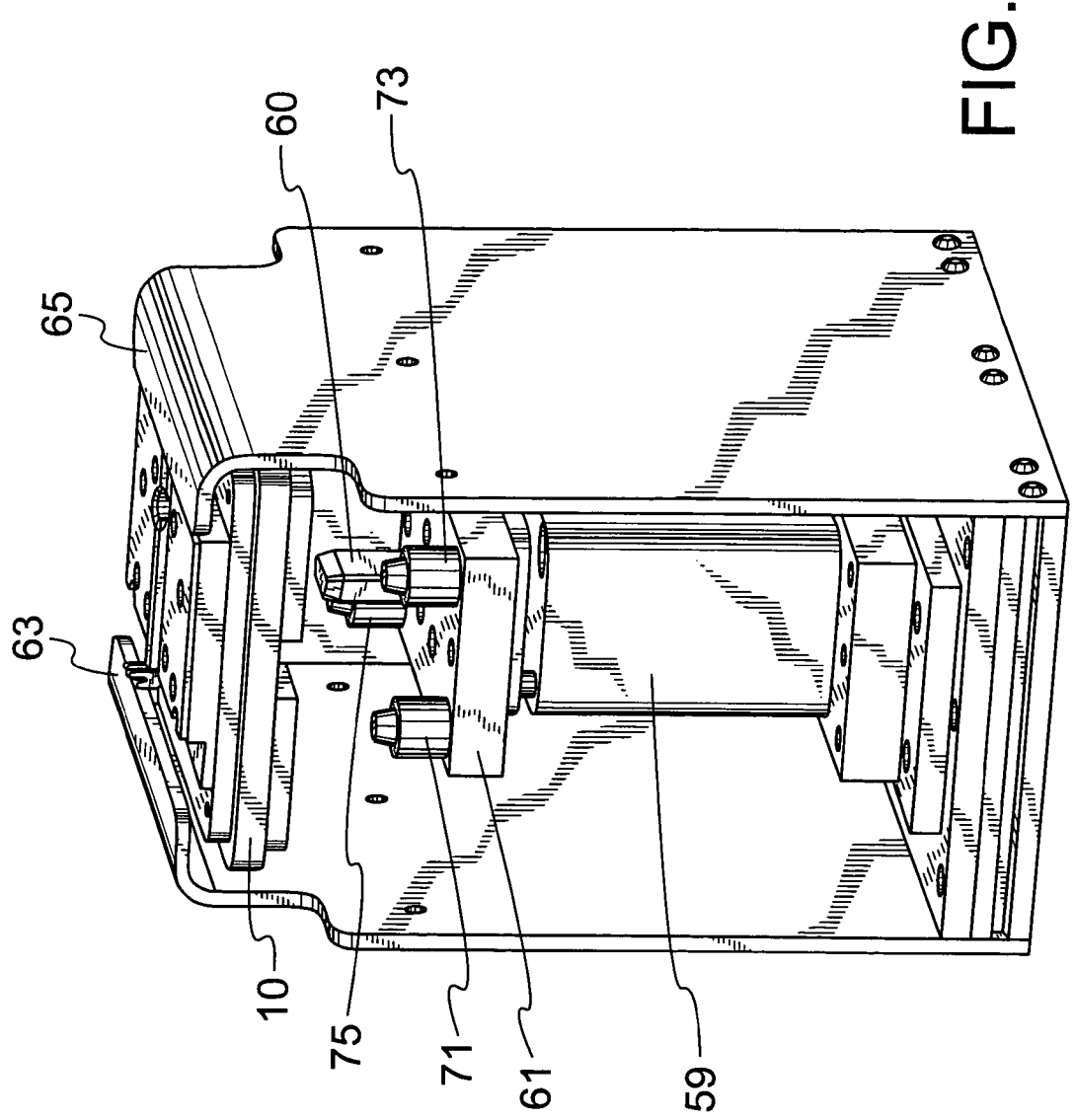
FIG. 8 is a view in perspective illustrating a preferred structure for displacing the lip members apart.
Figure 9:
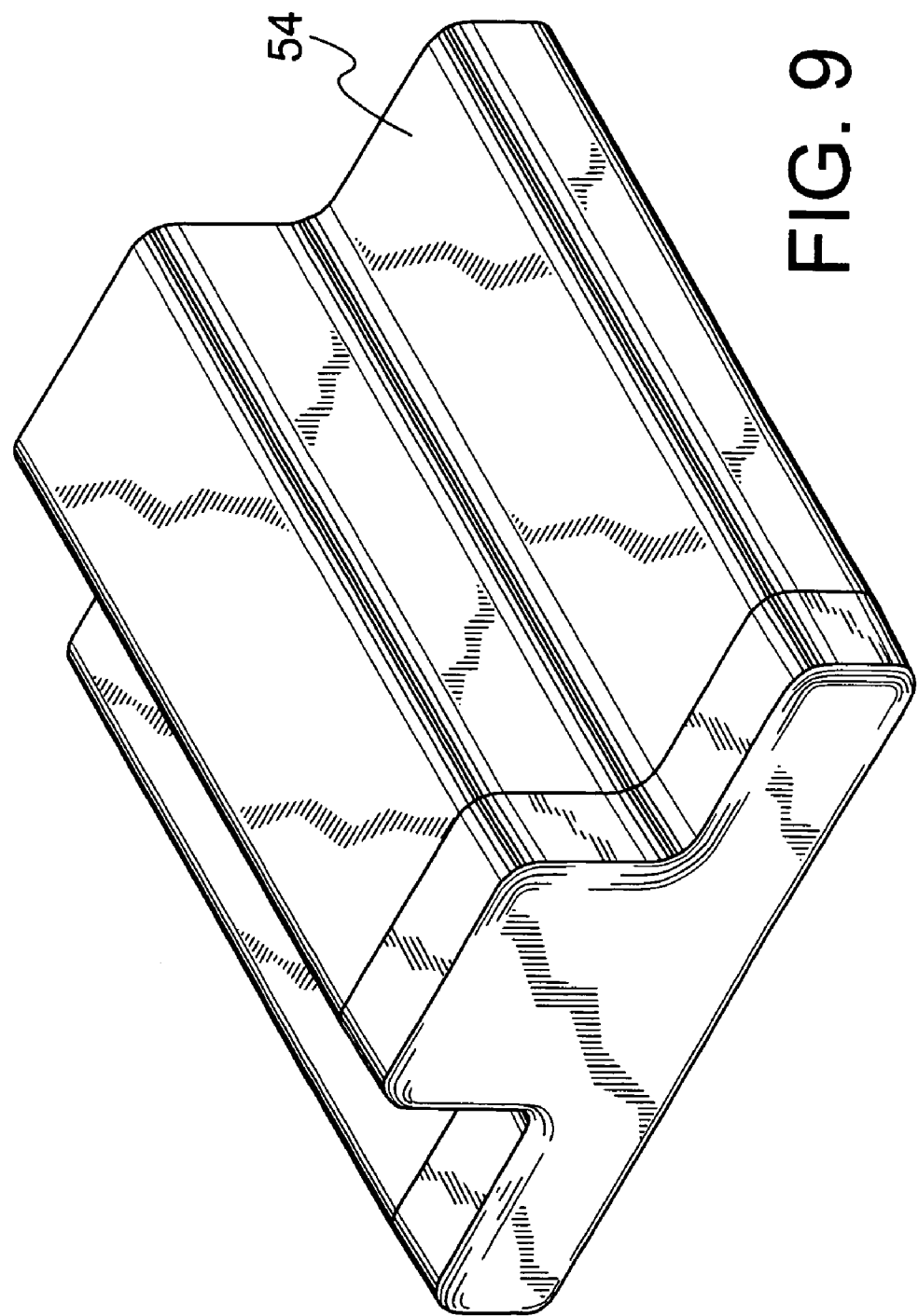
FIG. 9 is a view in perspective illustrating the T-shaped finger that extends into a recess near one end of the cartridge to positively position the cartridge in the pallet.

Before the pallet 10 is first loaded with a cartridge, the lips 26 and 28 are retracted by the structure shown in FIG. 8. The pallet 10 is lifted off of a conveyor on which it rests (not viable) by a prime mover, such as the pneumatic ram 59, which displaces the plate 61 upwardly. The plate 61 has rigidly mounted feet 71, 73, 75 (and another foot that is not visible in FIG. 8) that cooperate to align and lift the pallet 10 as described below. After the pallet 10 is lifted a predetermined distance, its upper surface seats against the undersides of the rigid flanges 63 and 65, which prevent any upward movement beyond the flanges.

Figure 3:
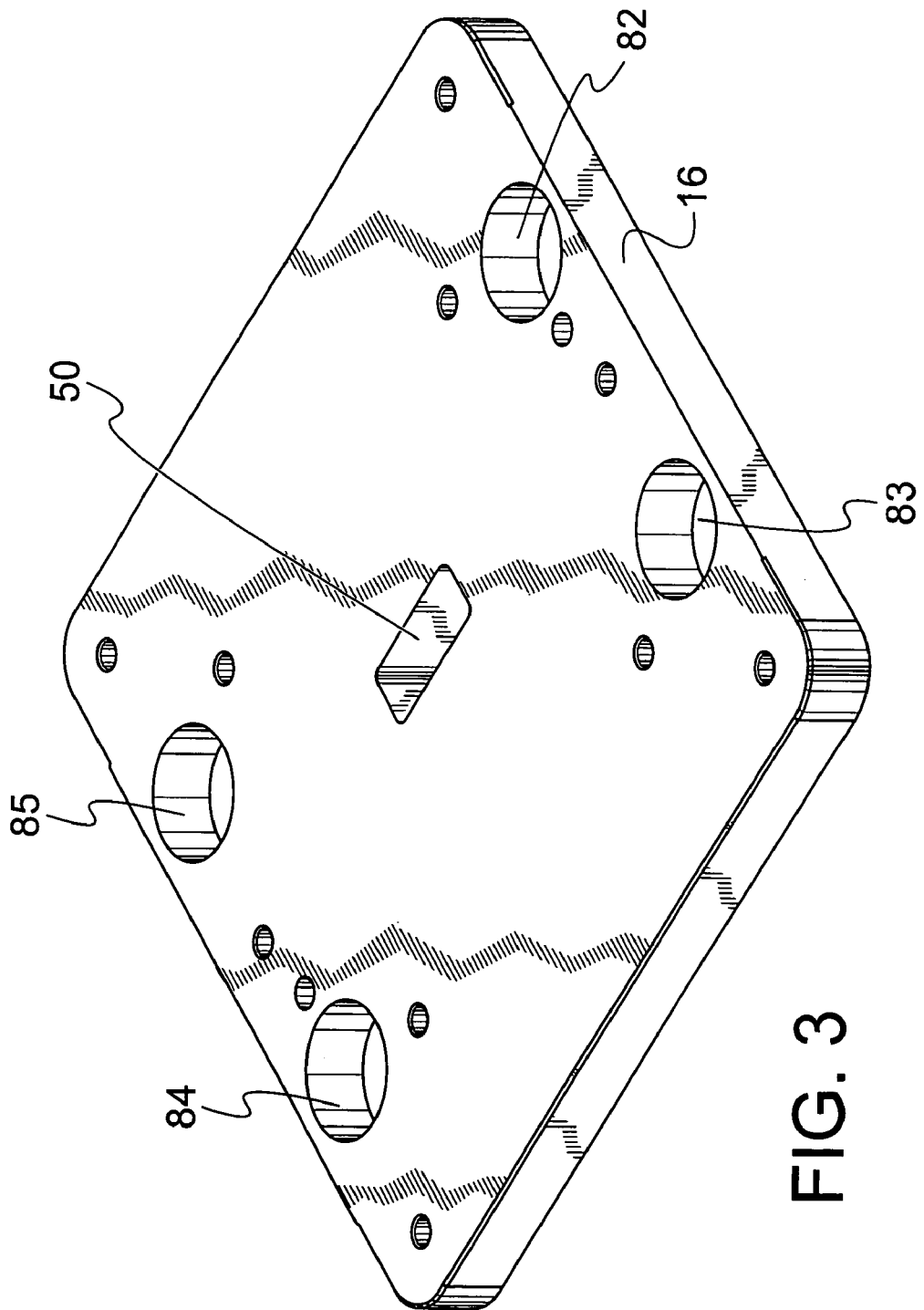
FIG. 3 is a view in perspective illustrating the plate, which is a component of the pallet.
Figure 4:
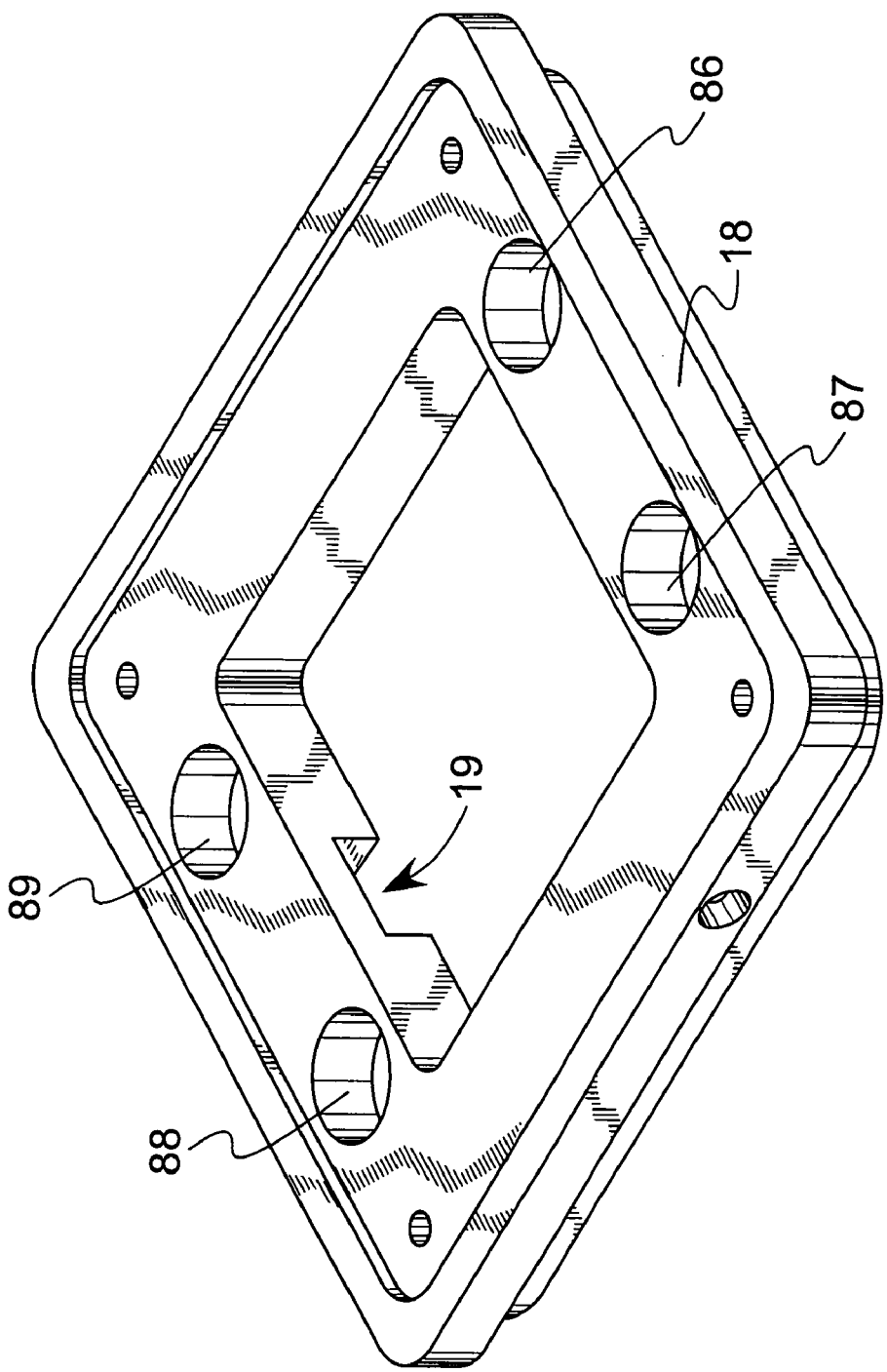
FIG. 4 is a view in perspective illustrating the ring, which is a component of the pallet.

Also rigidly mounted to the plate 61 is a tongue that is aligned with an aperture 50, shown in FIG. 3, formed through the plate 16. As the plate 61 is displaced upwardly before the feet contact the pallet, the tongue 60 extends through the ring 18, through the aperture 50 and through the aperture 52 of the cartridge holder 20 shown in FIG. 2. The edges of the tongue 60 seat against the opposed, tapered surfaces (surface 27 on lip member 22 and an essentially identical surface on lip member 24) of the lip members 22 and 24. This seating begins to displace the lip members outwardly away from the slot 40, and as the tongue is extended further into the aperture 52 and the feet contact the pallet 10, the tongue 60 further displaces the lip members 22 and 24 outwardly, thereby retracting the lips 26 and 28 from the slot 40. Once the lips 26 and 28 are no longer in the slot 40, the cartridge 12 can be inserted in the slot 40, and the tongue can be withdrawn, thereby permitting the biased lip members to be displaced inwardly to hold the cartridge 12.

Figure 6:
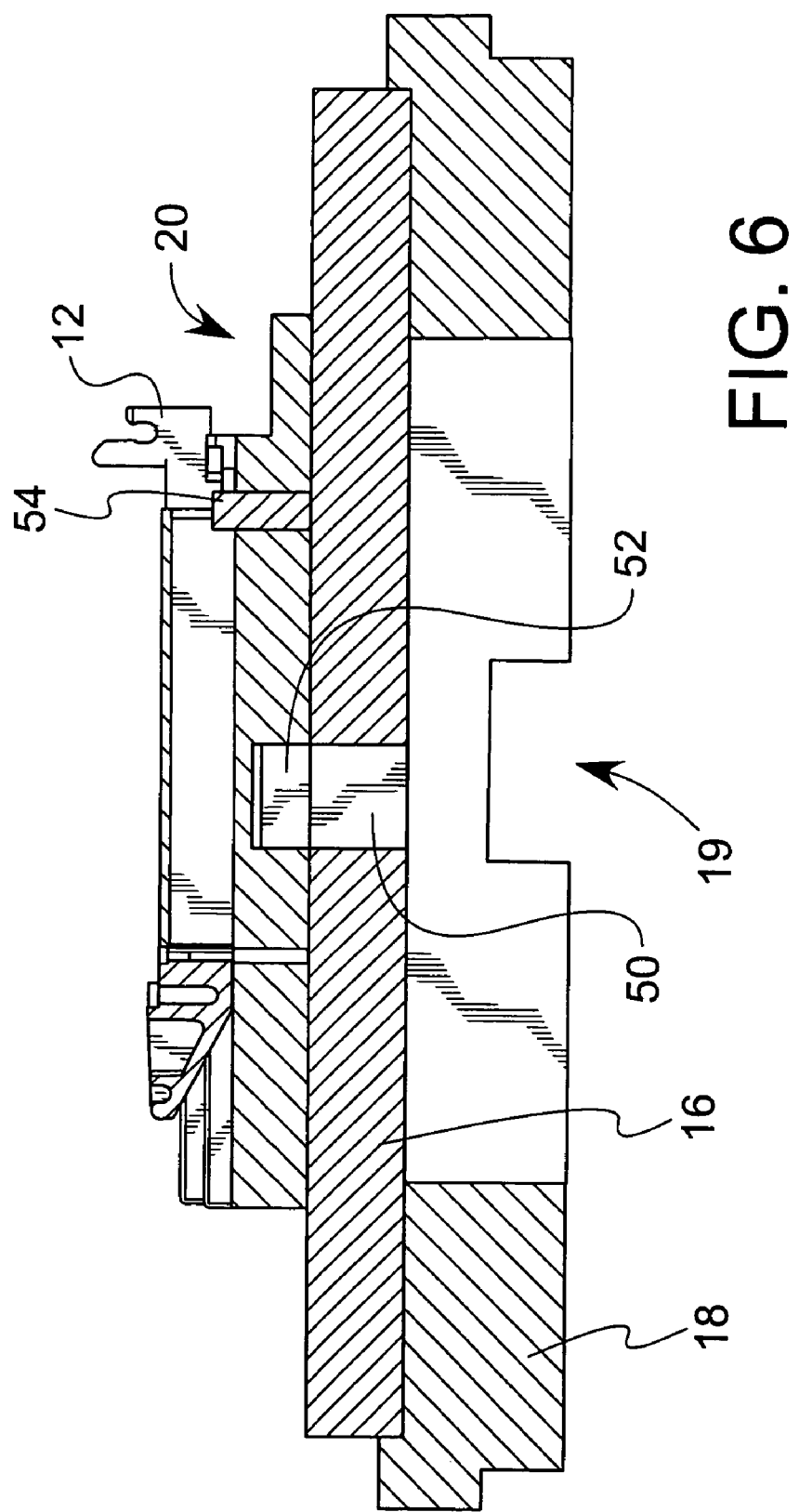
FIG. 6 is a side view in section through the line 6—6 of FIG. 1.
Figure 7:
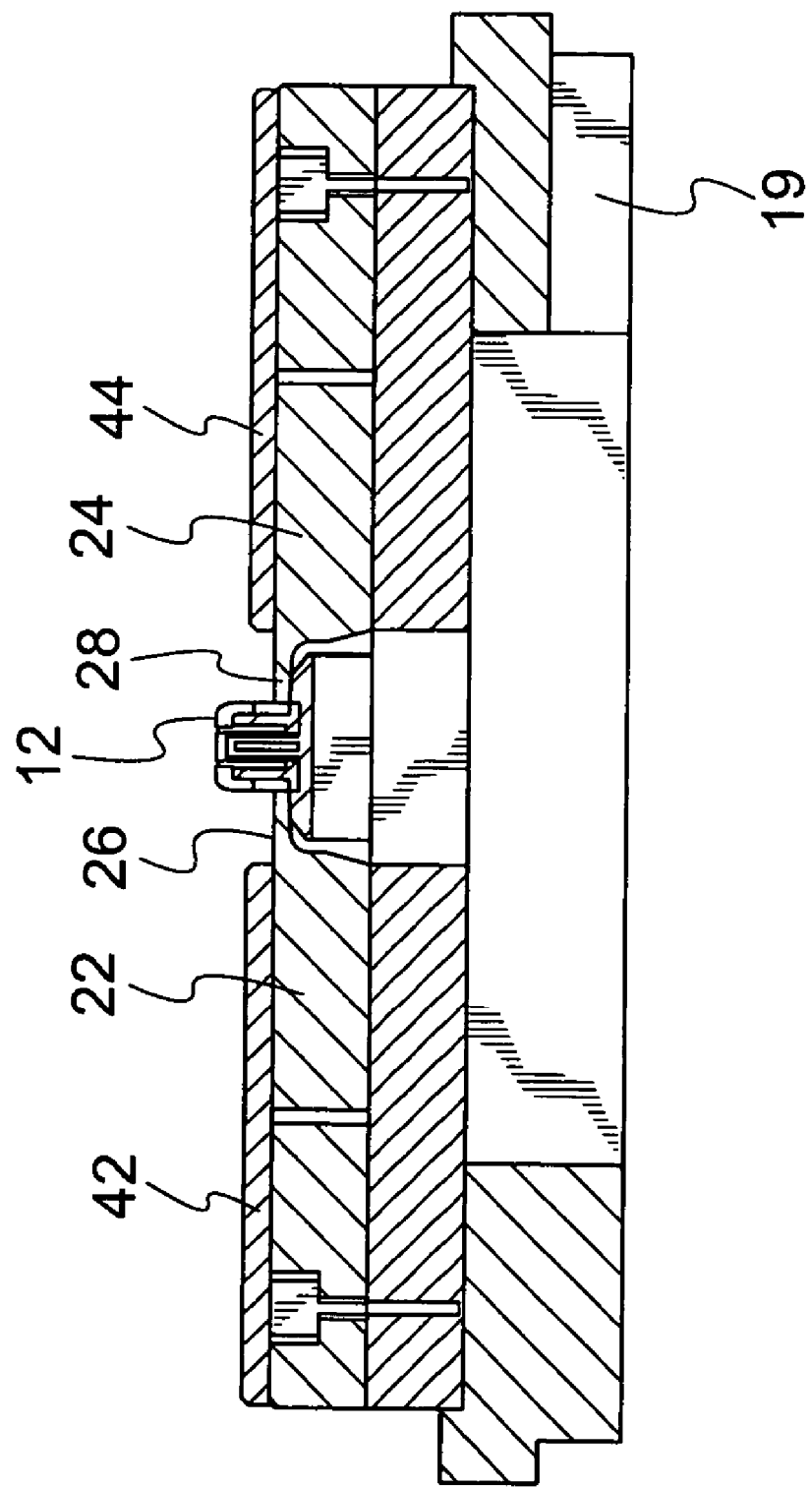
FIG. 7 is a side view in section through the line 7—7 of FIG. 1.

The cartridge 12 is thus held in the pallet 10 by the slot and the cartridge holding apparatus. However, the cartridge 12 must also be precisely positioned in the slot so that the apertures in the cartridge 12 are correctly positioned relative to the machines, described below, that insert drivers into the cartridge. The T-shaped finger 54 is mounted in the T-shaped opening 62 in the cartridge holder 20. The finger 54 extends upwardly into the slot, and when the cartridge is placed in the slot 40, the finger 54 extends into a recess formed in one end on the underside of the cartridge 12 as shown in FIG. 6. The finger 54 thus precisely positions the cartridge 12 in the slot 40 by restricting the cartridge's movement in the plane of the pallet 10. The lips 26 and 28 restrict movement of the cartridge 12 outside of the plane of the pallet 10.

Once the cartridge 12 is precisely positioned in the pallet 10, the pallet must be precisely positioned relative to each machine that operates on the cartridge 12. The pallet is preferably conveyed along by a conveyor system, such as a conventional conveyor sold by Flexlink AB. This conveyor transports pallets with cartridges between several stations, each station having a machine that inserts drivers or a swing tab into a cartridge. The machines are essentially conventional, as described herein and in the patents incorporated by reference. However, the cooperation of the pallets with the machines is not conventional, as described below.

At each station, the pallet 10 is halted by a retractable pin that extends into the path of the pallet 10 on the conveyor, thus preventing the passage of the pallet. The pin preferably extends upwardly and the pallet is stopped when the pallet's leading edge strikes the pin. The pin is positioned to stop the pallet when the pallet is positioned directly over the apparatus shown in FIG. 10, and directly below the apparatus shown in FIG. 11.

Figure 10:
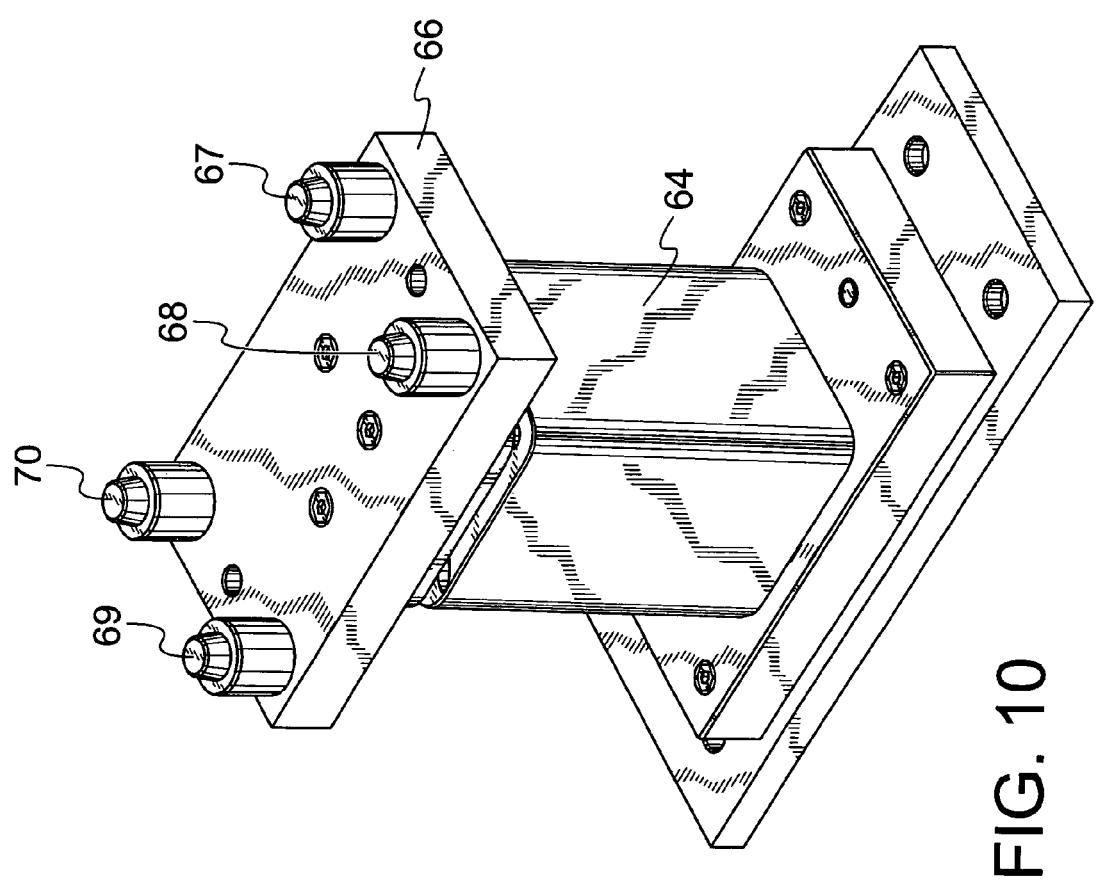
FIG. 10 is a view in perspective illustrating the preferred structure for lifting the pallet and horizontally aligning it relative to a machine.
Figure 11:
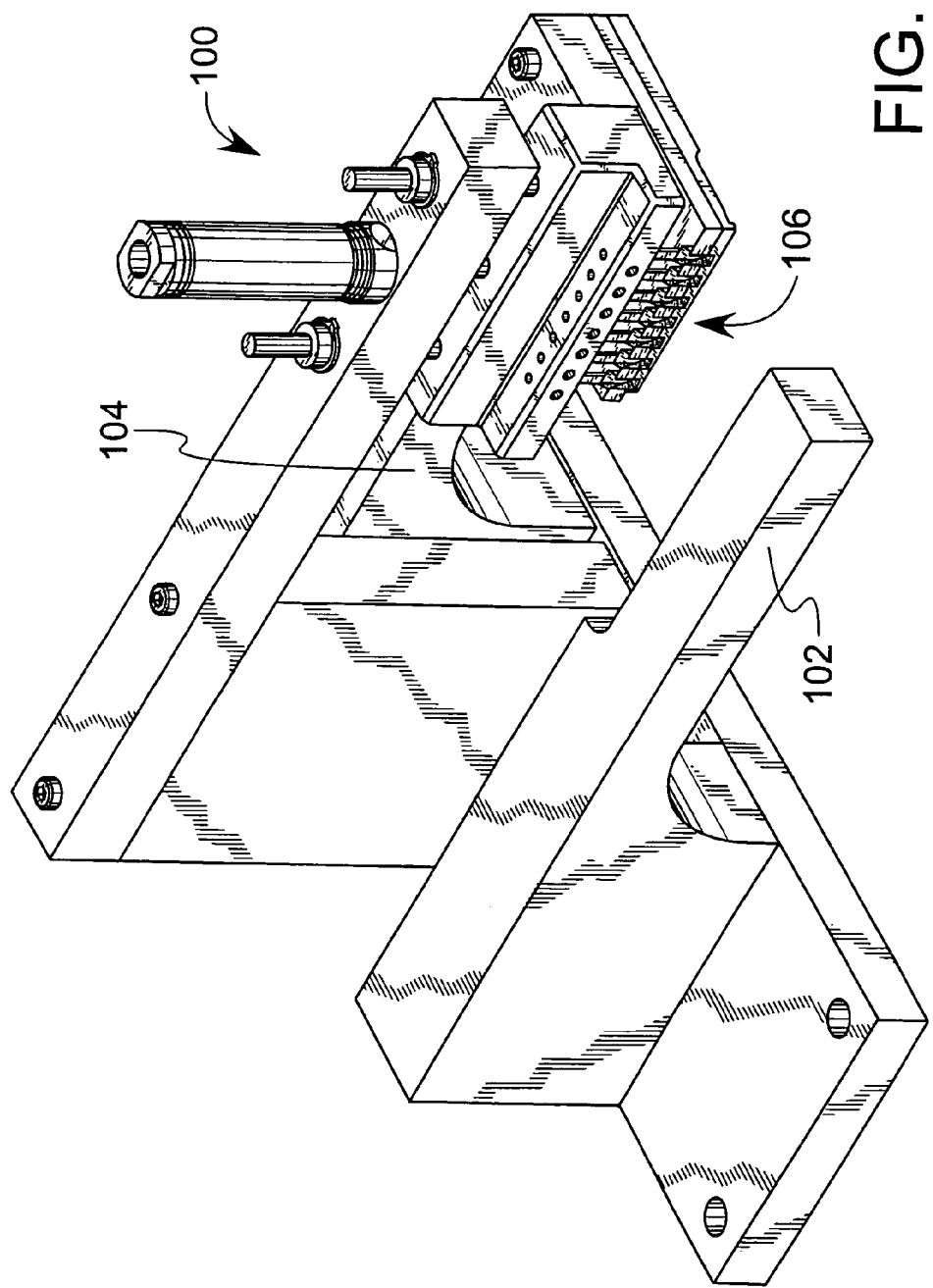
FIG. 11 is a view in perspective illustrating a preferred machine for inserting drivers into a cartridge, and a pair of cantilevered arms that define the upper limit of the pallet travel above the conveyor.
Figure 13:
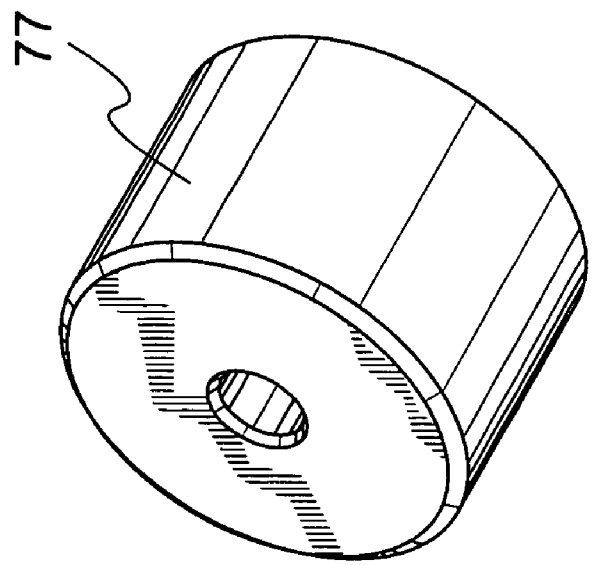
FIG. 13 is a view in perspective illustrating a preferred socket.
Figure 12:
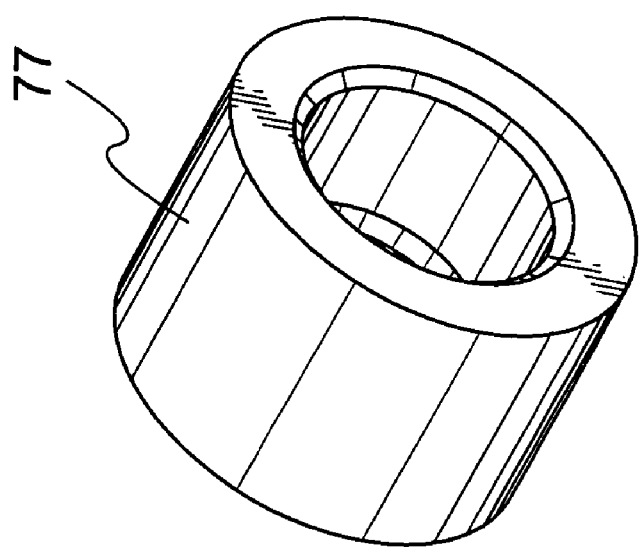
FIG. 12 is a view in perspective illustrating a preferred socket.

The apparatus shown in FIG. 10 includes a prime mover, which is preferably the pneumatic ram 64, that is drivingly linked to the plate 66. The plate 66 has four tapered feet 67, 68, 69, and 70. Corresponding to the feet 67–70 are the sockets 77, 78, 79 and 80, one of which is shown in FIGS. 12 and 13 and which is representative of all of the sockets 77–80. The sockets 77–80 are mounted to the pallet 10 by screws (not shown) extending through openings 77', 78', 79' and 80', respectively, shown in FIG. 2. The sockets 77–80 seat against the underside of the cartridge holding apparatus 20, and are contained within apertures 82, 83, 84 and 85, respectively, formed in the base 16, and apertures 86, 87, 88 and 89, respectively, formed in the ring 18.

The tapered cavities of the sockets 77–80 receive the tapered feet 67–70, respectively. Because the cavities and feet are tapered, a degree of initial misalignment does not cause the pallet to stay misaligned relative to the machine that will operate on the cartridge. The tapered structures permit the misalignment to be corrected as the plate 66 raises the pallet 10 off of the conveyor upwardly toward the machine 100 shown in FIG. 1. Any misalignment of the pallet 10 relative to the plate 66 disappears as the tapered surfaces of the feet and cavities slide relative to one another during lifting. Thus, once the feet 67–70 seat in the sockets 77–80, there is extremely precise alignment of the pallet 10 with the plate 66, thus precisely positioning the pallet 10 horizontally relative to the machine.

As the pallet 10 is raised up to the machine 100, the upper surface of the pallet 10, and preferably the tops of the cover panels 42 and 44, seat against the undersides of the cantilevered arms 102 and 104. The position of the pallet 10 when the top surfaces of the cover panels 42 and 44 seat against the arms 102 and 104 is precisely predetermined, so that when this seating occurs, the pallet 10, and the attached cartridge 12, are positioned for insertion of the drivers into the cartridge. Thus, the cooperation between the tapered feet and the tapered cavities registers the horizontal position of the pallet 10 relative to the machine 100 as described above, and the cooperation between the upper surfaces of the cover panels 42 and 44 and the cantilevered arms 102 and 104 registers the vertical position of the pallet 10 relative to the machine 100.

Once the pallet 10 is in the aligned position, the machine 100 functions in an essentially conventional manner to insert the drivers into the cartridge 12. As is known in the industry, such insertion ordinarily takes place in several stations, each of which inserts a fraction of the total number of drivers. Thus, once the first fraction of drivers is inserted, the ram 64 lowers the pallet 10 back onto the conveyor, the retractable pin retracts and the conveyor conveys the pallet 10 to the next station at which the process of lifting and inserting drivers is repeated, except that the next set of drivers is inserted.

The pallet 10 has a slot 19 in one side of the ring 18. The slot has a width and a depth that permits the pin that stops the pallet 10 to pass therethrough. This accommodates the action of the retractable pin, which is to retract momentarily when the pallet is supposed to be driven past the pin, and then protrude upwardly to its pallet stopping position even while the just-released pallet is still directly over the pin. The slot 19 passes directly over the pin, and therefore the pin has no effect on the pallet that was just released to be conveyed downstream. However, the pin does seat against and stop the leading edge of the next upstream pallet.

At some time drivers must be positioned in the machine 100 in order to be inserted by the machine into a cartridge. A plurality of drivers is commonly molded to a frame 108 during manufacture. The frame 108 is a convenient structure used to grasp the plurality of drivers, which are otherwise too small to conveniently grasp and manipulate individually by hand. Thus, the plurality of drivers attached to the frame 108 can be positioned by hand in the region 106 of the machine 100. Alternatively, the drivers can be positioned in the region 106 by a mechanism, such as a conventional robotic arm using a unique gripping tool.

Figure 15:
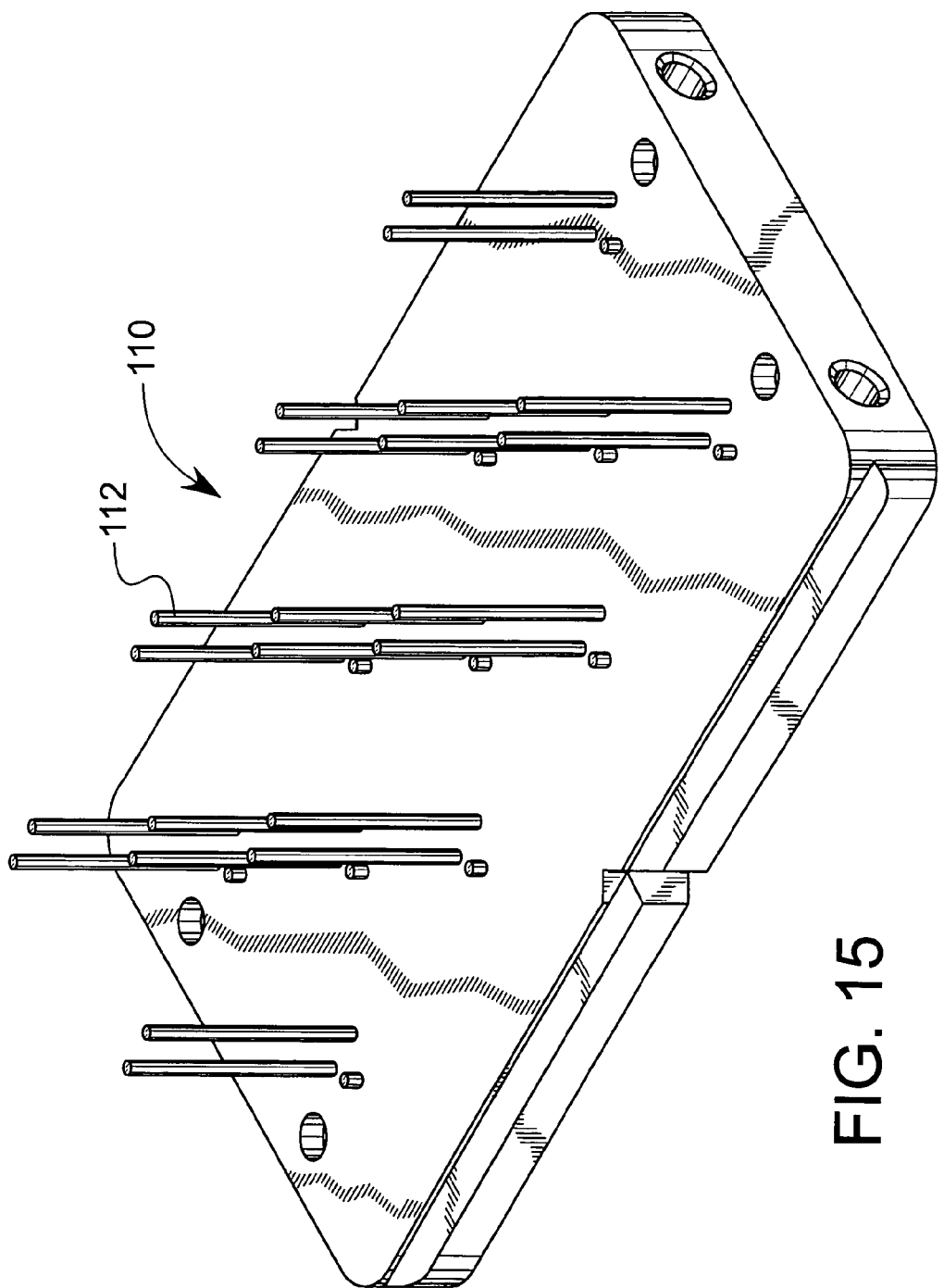
FIG. 15 is a view in perspective illustrating a preferred pallet for holding supplies, such as drivers.

In the preferred embodiment, many frames, such as the frame 108, are stacked on the rods 112 of the driver pallet 110, shown in FIG. 15. The frames are aligned by hand or by another robotic arm, so that a robotic arm can pick them individually off of the pallet 110 and place them in the region 106. A somewhat similar pallet 220 (FIG. 20) holds other supplies, such as swing tabs, which are installed in cartridges at another station. The tooling necessary to grasp the frames of the drivers and the swing tabs is especially designed to work with the frames, and is described next.

The end of arm tooling for the robotic arm is shown in FIG. 14 grasping the frame 108 between the tips of two fingers 114 and 116. The first finger 114 and the second finger 116 are drivingly linked to a prime mover, such as the servomotor of the robotic arm, which displaces the fingers 114 and 116 relative to one another. Of course, only one finger need be driven by the servomotor and the other could be merely connected to the robotic arm. The first finger 114 has an inwardly facing surface 124, and the second finger has an inwardly facing surface 126, which are preferably in close proximity to one another once the fingers grasp the frame 108 and the arm moves the frame 108 to the region 106.

The first finger 114 has a pair of transverse planar panels 130 and 131 formed in the inwardly facing surface 124 near the tip of the finger 114. The planar panels 130 and 131 are adapted to seat against the corresponding surfaces 130' and 131' on the driver frame as shown in FIG. 14.

The second finger has a pair of transverse planar panels 134 and 135 formed in the inwardly facing surface 126 near the tip of the finger 116. The planar panels 134 and 135 are adapted to seat against the corresponding surfaces 134' and 135' on the driver frame as shown in FIG. 14. By clamping the frame 108 between the fingers 114 and 116, the robotic arm can lift the frame 108 off of the pallet 110 and then move it over to the region 106 with precision. The precision arises from the exact registration of the transverse panels 130 and 131 seating against the corresponding surfaces 130' and 131'. Because the transverse panels 130 and 131 form a V-shaped structure, that structure seats precisely in the V-shaped intersection of the corresponding surfaces 130' and 131'. A similar result arises because of the planar panels 134 and 135 seating against the corresponding surfaces 134' and 135' of the frame 108.

There are also substantially parallel planar panels 132 and 133 that intersect the transverse planar panels 130 and 131, respectively, at the ends of the transverse planar panels 130 and 131 closest to the tip of the finger 114. These parallel panels 132 and 133 seat against the underside of the frame 108 to positively position it along the length of the finger 114. The substantially parallel panels 136 and 137 intersect the transverse planar panels 134 and 135, respectively, at the ends of the transverse planar panels 134 and 135 closest to the tip of the finger 116. This arrangement of planar panels provides precision in the position of the frame 108.

Figures 16, 17:
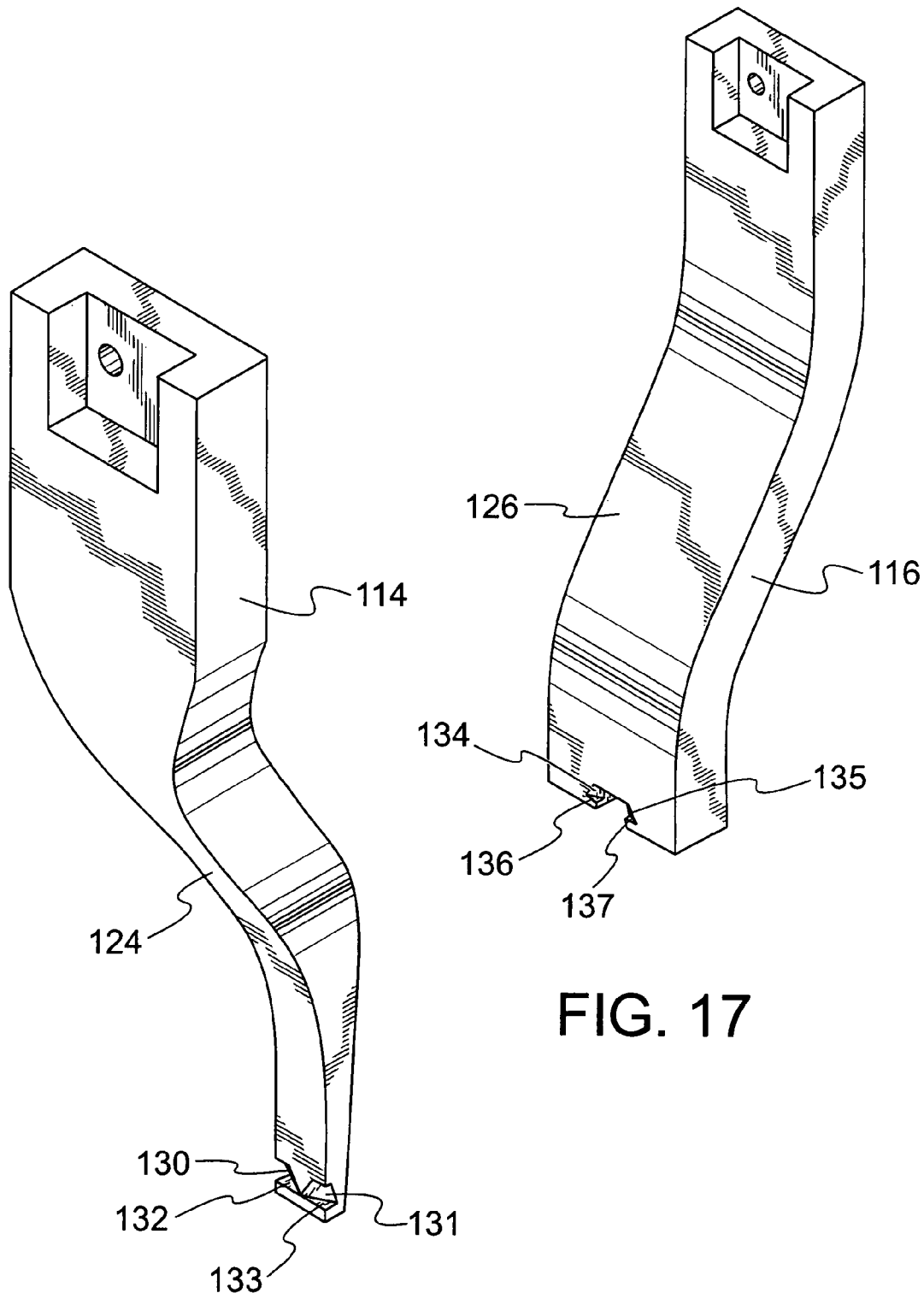
FIG. 16 is a view in perspective illustrating one finger of the special end of arm tooling.
FIG. 17 is a view in perspective illustrating a second finger of the special end of arm tooling.
Figure 18:
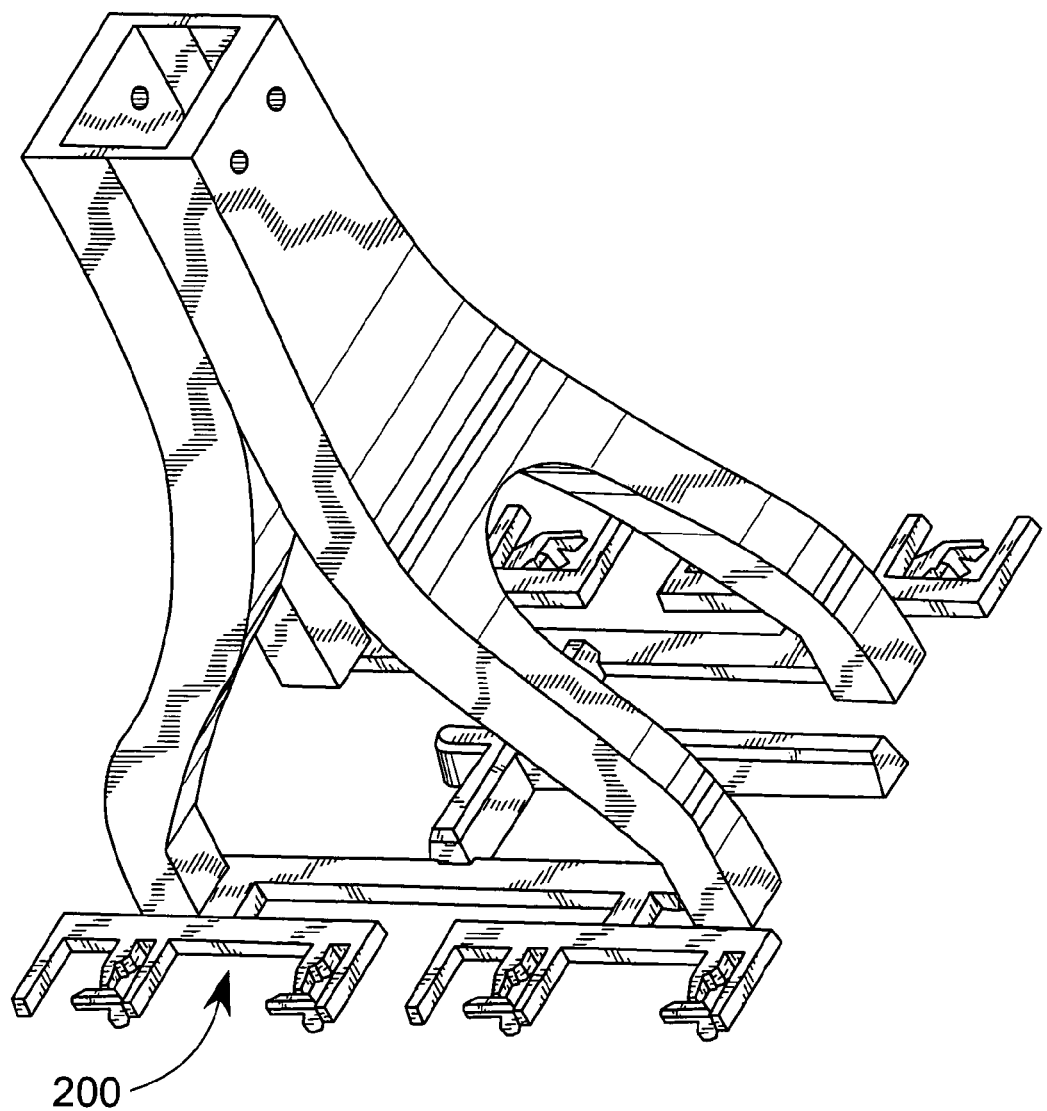
FIG. 18 is a view in perspective illustrating special end of arm tooling for gripping swing tab frames, and shows a swing tab frame in an operable position.
Figure 19:
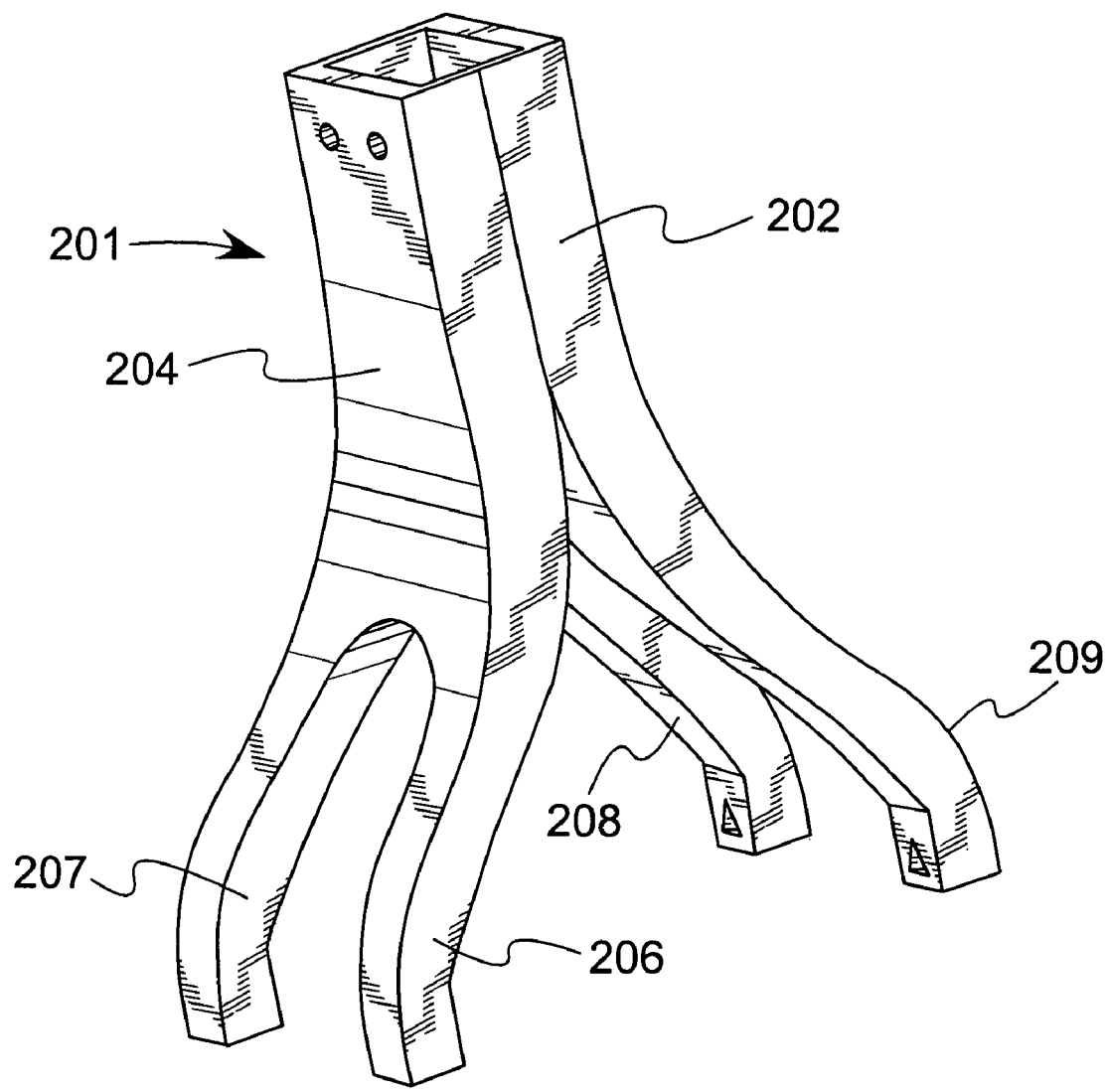
FIG. 19 is a view in perspective illustrating special end of arm tooling for gripping swing tab frames.
Figure 20:
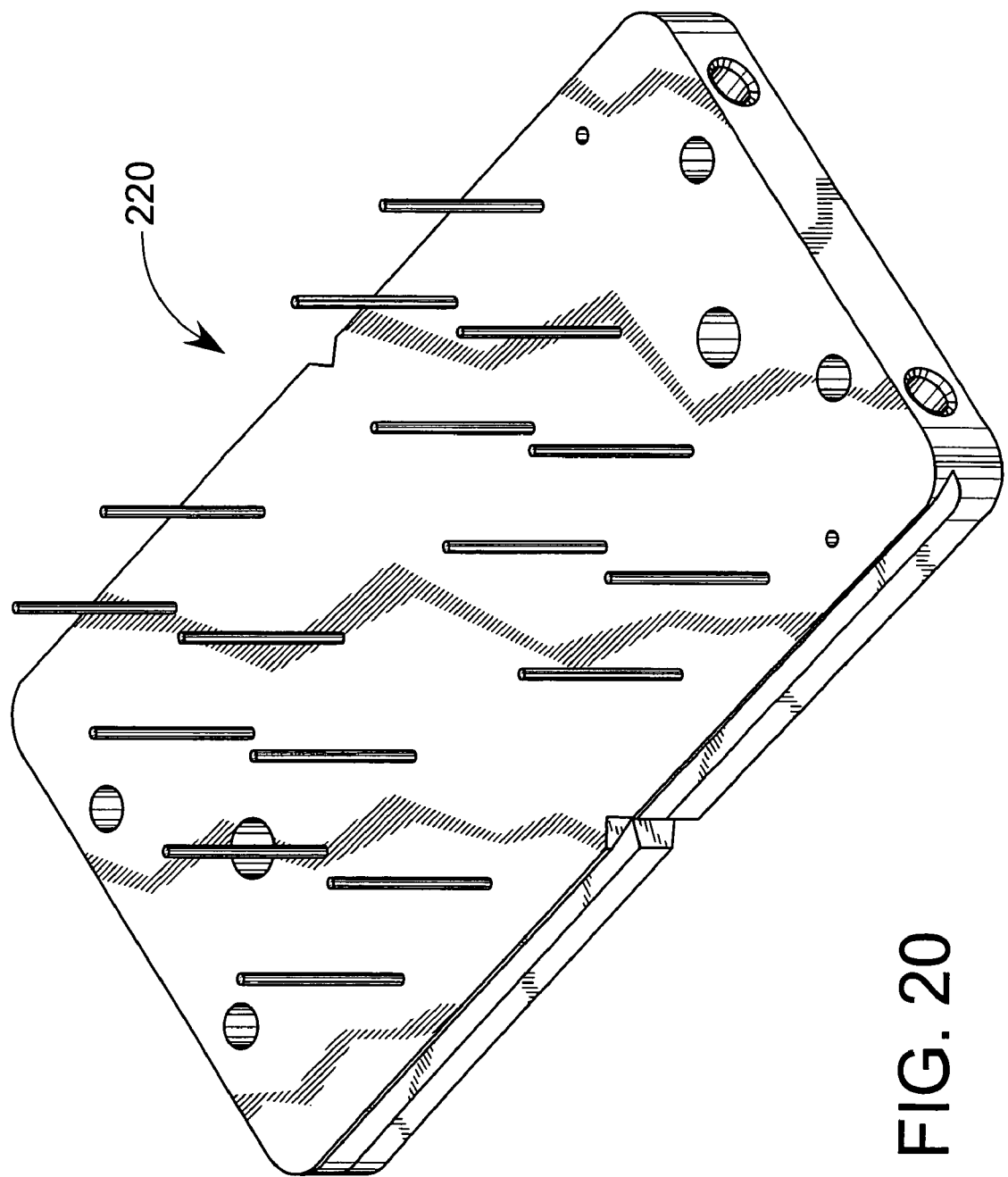
FIG. 20 is a view in perspective illustrating a preferred pallet for holding supplies, such as swing tabs.

The station in which swing tabs are inserted in the cartridges has an additional robotic arm that uses a special tool 201 to grip the swing tab frame 200, shown in FIGS. 18 and 19, and remove it from the pallet 220 shown in FIG. 20. The tool 201 has fingers 202 and 204, which are forked to form legs 206, 207, 208 and 209. The legs 206–209 have transverse planar panels formed in the fingers near the tips in which the angled ends of the swing tab frame 200 are inserted to grip the frame 200 as shown in FIG. 18. These transverse planar panels are substantially equivalent in function to the planar panels described above in association with FIGS. 14, 16 and 17. Thus, the angled ends of the swing tab frame 200 extend into the cavities formed by the transverse planar panels, and the fingers grip the frame 200 therebetween under the force of a prime mover, such as a servomotor on the robotic arm.

The entire process of putting cartridges in pallets, inserting drivers and swing tabs, and conveying the pallets is computer controlled, inasmuch as each pallet is conveyed by the conveyor, which is started and stopped (if necessary) by a central computer. Additionally, sensors at each station detect whether a pallet is present at each station by detecting a device mounted in the side of each pallet, such as the screw 150 in the pallet 10 (FIG. 1). When a pallet is detected, the computer actuates the pneumatic ram apparatus to raise the pallet to the position in which it can be operated on by the machine at that station. Once the machine is finished with its task, the computer actuates the ram to lower the pallet and the retractable pin is activated by the computer to be retracted to permit the pallet to be conveyed further by the conveyor. Essentially all functions are either controlled or monitored by the central computer. The only human monitoring, other than viewing the apparatus for malfunctions, is the placing of cartridges in the pallet initially, removing the finished cartridges from the pallets and placing supplies, such as driver frames and swing tab frames on the pallets that supply the robotic arms. However, it is contemplated that all of these functions could be mechanized.

While certain preferred embodiments of the present invention have been disclosed in detail, it is to be understood that various modifications may be adopted without departing from the spirit of the invention or scope of the following claims.

What is claimed is:

1. A moveable pallet for firmly holding a surgical stapling cartridge as drivers are inserted therein, the pallet comprising:
   (a) a base having a lower surface for seating on a conveyor, and an upper surface having an elongated cartridge region;
   (b) a first cartridge-retaining lip member movably mounted to the base on a first side of the cartridge region, said first lip member being biased toward the cartridge region and having a lip extending from the lip member into the cartridge region; and
   (c) a second cartridge-retaining lip member mounted to the base on a second side of the cartridge region, said lip member having a lip extending from the lip member into the cartridge region.

2. The pallet in accordance with claim 1, wherein the cartridge region is an elongated slot formed between the lip members for holding the cartridge.

3. The pallet in accordance with claim 2, wherein the second cartridge-retaining lip member is movably mounted to the base and biased toward the slot.

4. The pallet in accordance with claim 3, further comprising a gap formed between the first and second lip members and adapted to receive a tongue that is inserted upwardly through an aperture in the base and seating against opposing surfaces of the lip members and displacing the lip members away from the slot.

5. The pallet in accordance with claim 3, further comprising a finger mounted to the base near a first longitudinal end of the slot, said finger extending upwardly from the base for seating in a recess of said cartridge.

6. The pallet in accordance with claim 5, wherein the lip members are slidably mounted within chambers formed in the base.

7. The pallet in accordance with claim 6, further comprising chamber cover panels mounted to the base over the chambers, said chamber cover panels having upper surfaces.

8. The pallet in accordance with claim 7, wherein said cover panel upper surfaces define seating surfaces for seating against stops and vertically positioning the pallet.

9. The pallet in accordance with claim 5, further comprising at least one tapered cavity formed in the lower surface of the base for receiving a tapered tip and horizontally positioning the pallet.

10. A moveable pallet for firmly holding a surgical stapling cartridge as drivers are inserted therein, the pallet comprising:
    (a) a base having a lower surface for searing on a conveyor;
    (b) an elongated slot formed in an upper surface of the base for holding the cartridge;
    (c) a first cartridge-retaining lip member movably mounted to the base on a first side of the slot, said first lip member being biased toward the slot and having a lip extending into the slot;
    (d) a second cartridge-retaining lip member movably mounted to the base on a second side of the slot, said second lip member being biased toward the slot and having a lip extending into the slot;
    (e) a gap formed between the first and second lip members and adapted to receive a tongue inserted upwardly through an aperture in the base, for seating against opposing surfaces of the lip members and displacing the lip members away from the slot; and
    (f) a finger mounted to the base near a first longitudinal end of the slot, said finger extending upwardly from the base for seating within a recess of said cartridge.

11. The pallet in accordance with claim 10, further comprising first and second chambers formed in the base on first and second sides of the slot, respectively, said first and second chambers housing the first and second lip members, respectively.

12. The pallet in accordance with claim 11, further comprising at least one tapered cavity formed in the lower surface of the base for receiving a foot for positively positioning the pallet horizontally.

13. The pallet in accordance with claim 12, further comprising at least one vertical registration surface for seating against at least two registration arms for positively positioning the pallet vertically.

14. The pallet in accordance with claim 13, further comprising chamber cover panels mounted to the base over the chambers, wherein upper surfaces of the cover panels comprise said at least one vertical registration surface.

* * * * *

UNITED STATES PATENT AND TRADEMARK OFFICE
CERTIFICATE OF CORRECTION

PATENT NO. : 6,973,770 B2
DATED : December 13, 2005
INVENTOR(S) : Ronald J. Schnipke et al.

It is certified that error appears in the above-identified patent and that said Letters Patent is hereby corrected as shown below:

<u>Column 8,</u>
Line 14, add -- seating --, delete "searing".
Line 35, insert -- the -- between "on" and "first".

Signed and Sealed this

Fourteenth Day of February, 2006

JON W. DUDAS
*Director of the United States Patent and Trademark Office*